United States Patent [19]

Wu et al.

[11] Patent Number: 4,837,004

[45] Date of Patent: Jun. 6, 1989

[54] RUMEN-STABLE PELLETS

[75] Inventors: Stephen H. W. Wu, Kingsport; Shane K. Kirk, Church Hill; Kenneth P. Perry, Kingsport; E. Phillip Smith, Blountville; Yeong-Ho Chang; Waylon L. Jenkins, both of Kingsport, all of Tenn.

[73] Assignee: Eastman Kodak Company, Rochester, N.Y.

[21] Appl. No.: 150,180

[22] Filed: Jan. 29, 1988

Related U.S. Application Data

[63] Continuation-in-part of Ser. No. 789,282, Oct. 18, 1985, abandoned, which is a continuation-in-part of Ser. No. 498,445, May 26, 1983, abandoned, and a continuation-in-part of Ser. No. 688,387, Jan. 2, 1985, abandoned.

[51] Int. Cl.$^4$ .......................... A61K 9/22; A61K 9/32; A61K 9/36
[52] U.S. Cl. ...................................... 424/438; 524/37; 524/38
[58] Field of Search ...................... 524/37, 38; 424/21, 424/32, 35, 38

[56] References Cited

U.S. PATENT DOCUMENTS 4,181,708  1/1980  Dannelly .............................. 424/19
4,181,709  1/1980  Dannelly .............................. 424/19

*Primary Examiner*—John Kight
*Assistant Examiner*—Nathan M. Nutter
*Attorney, Agent, or Firm*—Thomas R. Savitsky; William P. Heath, Jr.

[57] ABSTRACT

Coating compositions and pellets coated therewith which are adaptable for oral administration to ruminants are disclosed. The coating protects the core material of the pellets in the rumen and releases it postruminally. The coating is a specific mixture of a film-forming polymeric material, hydrophobic material and flake material.

43 Claims, 2 Drawing Sheets

RUMEN-STABLE PELLETS

This application is a continuation-in-part of application Ser. No. 789,282 filed Oct. 18, 1985 and now abandoned, which is a continuation-in-part of application Ser. No. 498,445 filed May 26, 1983, now abandoned, and Ser. No. 688,387 filed Jan. 2, 1985, now abandoned.

TECHNICAL FIELD

This invention relates in general to pellets adapted to be orally administered to ruminants and which are beneficial to ruminants after passing the rumen and reaching the abomasum and/or intestines. More particularly, this invention relates to pellets having, in terms of structure, a core material such as a nutrient or medicament and a coating over the core material which protects the core in the environment of the rumen, but which loses continuity under the more acidic conditions of the abomasum to render the core material available for utilization by the animal.

BACKGROUND OF THE INVENTION

In ruminants, e.g., beef and dairy cattle, sheep, etc., ingested feed first passes into the rumen, where it is pre-digested by fermentation. During this period of fermentation the ingested feed may be regurgitated to the mouth where it is salivated and ruminated. After a period of fermentation, absorption of digested nutrients starts and continues in the subsequent sections of the digestive tract. This digestive process is described in detail by D. C. Church, "Digestive Physiology and Nutrition of Ruminants", Vol. 1, O.S.U. Book Stores, Inc., of Corvallis, Oreg.

The rumen serves as an important location of metabolic breakdown of ingested foodstuffs through the action of microorganisms which are present therein. Ingested food is typically retained in the rumen for from about 6 to about 30 hours, during which time it is subject to metabolic breakdown by the rumen microorganisms. When the rumen contents pass into the abomasum and intestine, the microbial mass is digested, thus providing protein to the ruminant. Thus, the natural nutritional balance of the ruminant animal is primarily a function of the microbial composition and population.

In preparing nutrients and medicaments intended for administration to ruminants, it is important to protect the active ingredients against the environmental conditions of the rumen, i.e., microbial degradation and the effects of a pH of about 5.5, so the active substance will be saved until it reaches the particular location where adsorption takes place. It is well known that the rate of meat, wool and/or milk production can be increased if sources of growth limiting essential amino acids, and/or medicaments, are protected from alteration by microorganisms in the rumen and become available for direct adsorption by the animal later in the gastrointestinal tract.

Materials which protect the core against degradation by the rumen contents should be resistant to attack by the rumen fluid but must make the active ingredient available rapidly in the more acidic fluid of the abomasum (postruminally) at a pH within the normal physiological range of about 2 to about 3.5.

Because proteins are subject to breakdown in the rumen, it has been suggested that protein-containing nutrients fed to ruminants be treated so as to permit passage without microbial breakdown through the rumen to the abomasum. Suggested procedures have included coating the protein material, for example, with fats and vegetable oils; heat treating of the protein material; reacting the protein material with various compounds such as formaldehyde, acetylenic esters, polymerized unsaturated carboxylic acid or anhydrides and phosphonitrilic halides, etc.

It is likewise well-known that some medicaments are more effective when they are protected from the environment of the rumen. See, for example, U.S. Pat. Nos. 3,041,243 and 3,697,640.

Compositions containing nutrient and medicaments for administration to ruminants must also exhibit adequate stability upon storage. In particular, such compositions must retain sufficient activity when stored in high humidity and/or heat so that the compositions will be effective for their intended purpose. In addition, such compositions must be stable when in contact with moist feed.

In accordance with the present invention, a polymeric coating having a hydrophobic substance and a flake material dispersed therein, which coating is resistant to environmental conditions of the rumen but releases the core material under the environmental conditions of the abomasum, provides a very desirable utilization efficiency by ruminants. The core material may also contain a neutralizer to provide a pH above about 5.5.

The coating material has the ability to withstand environmental conditions of the rumen, and the ability to expose the core material of the pellet in the environment of the abomasum. Thus, the coating material is resistant to pH conditions of about 5.5 for at least about 24 hours. The coating material releases the core material upon exposure to post-ruminal environmental conditions having a pH of about 3.5 after a time of about 5 minutes to about 6 hours. The exposure of the core may occur by the coating becoming permeable to the fluids therein or by dissolving or disintegrating. Another requirements for the coating material is to have the ability to withstand feed environment or storage conditions of relatively high heat and/or humidity without a significant loss of rumen-stable and post-rumen release properties.

U.S. Patents of interest includes U.S. Pat. Nos. 3,619,200; 3,880,990; 3,041,243; 3,697,640; 3,988,480; 3,383,283; 3,275,518; 3,623,997; 3,073,748; 3,829,564; 3,832,252; and 3,917,813.

Of particular interest are U.S. Pat. Nos. 4,181,708; 4,181,709; and 4,181,710. The disclosure of U.S. Pat. No. 4,181,708 is incorporated herein by reference. The '708 patent discloses rumen-stable pellets coated with a mixture of a polymeric material, a hydrophobic material, and a flake material, and the '710 patent discloses rumen-stable pellets coated with a mixture of polymeric material, hydrophobic material and inert filler. It has, however, been unexpectedly discovered that when the nutrients and/or medicaments of the core are highly water soluble (such as glucose and lysine which have a solubility of more than 60 gm/100 gm water at 25° C.) excellent results are obtained when the hydrophobic material and flake material are present in amounts as described herein. In addition, it has been unexpectedly discovered that when the glass transition temperature (Tg) values of the coating compositions are as described herein, said compositions have increased stablity to heat and/or high humidity.

BRIEF DESCRIPTION OF THE DRAWINGS

FIG. 1 is a triangular coordinate graph illustrating the invention. The apex of the graph represents 100 weight % polymeric material, exemplified by 2-methyl-5-vinyl-pyridine/styrene (80:20). The lower right corner of the graph represents 100 weight % flake material, exemplified by talc/- aluminum flake (50:50). The lower left corner of the graph represents 100 weight % hydrophobic material, exemplified by stearic acid. Compositions containing various concentrations of these three ingredients are represented graphically at A, B, C, D, and E, and the points labeled with a numerical figure. Such triangular coordinate graphs and their use are well known by those skilled in the art.

FIG. 2 is an enlarged section of the graph of FIG. 1 illustrating the present invention. The additional points not shown in FIG. 1, i.e., A', B', F, G, and H also represent various concentrations of the three ingredients as in FIG. 1. Lines of the graph representing major increments are also labeled.

SUMMARY OF THE INVENTION

According to the present invention, there are provided coating compositions and pellets adapted for oral administration to ruminants. The pellets comprise a core material beneficial to the ruminants postruminally (e.g., abomasum and intestine), and a coating surrounding the core material which protects the core material in the rumen and releases it post-ruminally. The coating comprises (a) a physiologically acceptable film-forming polymeric material comprising a polymer or a mixture of polymers, the polymeric material having basic amino groups the nitrogen content of which constitutes between about 2 and about 14% by weight of the polymeric material.

(b) between 1.5% and 121%, based on the weight of polymeric material, of a hydrophobic material dispersed in the polymeric material selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and (c) greater than about 200% and up to 485%, based on the weight of said polymeric material, of a physiologically acceptable flake material dispersed in the polymeric material.

The polymeric material in combination with the hydrophobic material and flake material is physiologically acceptable and resistant to a pH of greater than about 5 but capable of releasing the core of the pellets at a pH of less than about 3.5. The coating makes up about 5 to about 50% of the weight of the pellet. The coating has a glass transition temperature of to more than about 60° C. and said coating is further defined in terms of weight of the polymeric material, hydrophobic material and flake material by lines AB, BE, ED, DC, and CA of the tri-component graph of FIG. 1.

DETAILED DESCRIPTION OF THE INVENTION

Pellets

The pellets according to this invention are adapted for oral administration to ruminants. The pellets are of a suitable shape and size, such as cylindrical, having a diameter of about 1.0–2.0 mm and a length-to-diameter ratio of about 1–2.0:1. Also, the pellets must be of suitable density, i.e., a specific gravity of between about 1 and 1.7, have acceptable odor, taste, feel, etc. The pellets include a core and a continuous, film or coating completely encapsulating the core.

Core Material

The core is a material beneficial to the ruminant upon passing the rumen and reaching the abomasum and/or intestine. Normally, the core is a solid material which has been formed into particles, such as by pelletizing prior to being coated. The cores should have sufficient body or consistency to remain intact during handling, particularly during the coating operation. Suitable core materials include various medicaments and nutrients such as, for example, antibiotics, relaxants, drugs, antiparasites, amino acids, proteins, sugars, carbohydrates, etc. The core may also contain inert filler material such as clay and acid or base neutralizers.

The core material may be made ready for coating by the following method. The nutrient, medicament, or the like, and core neutralizer, if used, are mixed with water, binders, and sometimes inert organic substances added to adjust the specific gravity of the pellet and the resulting plastic dough-like mass is extruded or rolled to obtain suitable size particles. Adhesive binders may be added to strengthen the pellets and can be nontoxic vegetable gums, starches, cellulose derivatives, animal gums and other similar substances well-known in the art of food thickening and tablet making. Inorganic additives used to adjust the specific gravity of the pellet include such substances as insoluble, nontoxic pigment-like materials such as metal surfaces, oxides and carbonates having a relatively high density. After creating suitable size pellets, the pellets are dried to remove the water. The pellets are then coated by contacting them with a solution of the protectve coating material in a suitable solvent or mixture of solvent as hereinafter described.

Coating

The coating material is capable of forming a continuous film around the core by the evaporation of solvent from the coating material. It has the ability to withstand environmental conditions of the rumen, and the ability to expose the core material of the pellet in the environment of the abomasum. Thus, the coating material should be resistant to pH conditions of greater than about 5 for from about 6 to about 30 hours. The coating should release the core material after exposure to abomasum environmental conditions having a pH of about 2 to about 3.3. Release should occur within the residence time in the abomasum or later in the intestinal track but at least within a time period of six hours after contacting pH 3.5 or less. The exposure of the core may occur by the coating becoming permeable to the contents of the rumen, such as by dissolving, disintegrating, or extensive swelling. The coating material is physiologically acceptable, i.e., the coating material should not interfere with the ruminants' healthy or normal body functioning.

Another requirement for the coating material is its ability to withstand abrasion in handling and storage conditions of relatively high heat and/or humidity without a significant amount of blocking or sticking. Also, the coating material is preferably soluble or dispersable in organic solvents having boiling points of between about 40° and 140° C. to permit conventional coating processes such as spray coating to be used. Particularly suitable solvents include methylene chloride, chloroform, ethanol, methanol, ethyl acetate, acetone, toluene, isopropanol or mixtures of these.

Polymer

The polymer substances include homopolymers, copolymers, terpolymers, polymers having more than three monomers, and mixtures thereof having basic amino groups in which the nitrogen content of the polymeric substance is between about 2 and about 14% and of a film-forming molecular weight. As used herein the term "polymer" encompasses homopolymers, copolymers, terpolymers, and polymers made from more than three monomers. The basic amino groups may be of the aliphatic type in which case they will contain from about 2% to about 10% by weight of nitrogen in the basic amino groups. The basic amino groups may also be of the aromatic type in which the basic amino groups are attached directly to the aromatic ring, or are part of the aromatic ring structure in which case they will contain from about 6% to about 14% nitrogen in the basic amino groups. The polymeric substances are of sufficient molecular weight ot have film-forming properties when the polymer is deposited from a solution or dispersion and after removal of a solvent or dispersing medium, or on cooling from a melt.

Polymeric substances having the characteristics defined herein include certain modified natural polymers, homo- and interpolymers obtained by addition polymerization methods, homo- and copolymers obtained by condensation polymerization methods and mixtures thereof. The polymeric material is comprised of at least one polymer or blend of polymers comprising cellulose derivatives such as cellulose propionate morpholinobutyrate; containing addition-type monomeric moieties such as acrylonitrile; vinylated derivatives of pyridine; styrene; methylstyrene; vinyl toluene; esters and amides of methacrylic acid; acrylic acid; such as a dialkylamino ethyl acrylate or methacrylate in which the alkyl group contains from 1 to 6 carbon atoms, polymerizable ethylenically unsaturated aliphatic hyrocarbon monomers such as ethylene, propylene or butadiene; vinyl esters such as vinyl acetate, vinyl propionate or vinyl stearate; vinyl esters such as methyl, ethyl, propyl or stearyl, vinyl substituted heterocyclic ring or condensed ring compounds containing basic nitrogen configurations such as vinyl carbazole, vinyl quinoline, N-vinylpyrrole and 5-vinyl pyrozoline; containing condensation-type polymers wherein diacids such as phthalic, terephthalic, and succinic are combined with polyfunctionals alcohols to form polyesters wherein either the acid or glycol moiety may contain basic nitrogen reactive to variable pH environments and wherein the same or similar diacids may be reacted with polyfunctional amines to form polyamide-type polymers containing basic nitrogen not reacted in the polymerization process; and other basic nitrogen containing polymers such as polymers which have been formed by reacting an existing polymer with a nitrogen containing organic or inorganic moiety such as polybutadiene to which ammonia has been reacted with the remaining double bond. Especially preferred are poly(vinylpyridine), polymeric derivatives of vinylpyridine, and the copolymers of the various isomers and derivatives of vinylpyridine copolymerized with one or more of the above-mentioned addition type monomers.

Included among the especially preferred copolymers are 2-methyl-5-vinylpyridine and styrene, and in particular, the copolymer of about 75-85% by weight 2-methyl-5-vinylpyridine and about 15-25% by weight styrene, as well as the copolymer of 55-65% by weight 2-methyl-5-vinylpyridine and about 35-45% by weight acrylonitrile. Also especially preferred is the copolymer of 60-85 weight % 2-vinylpyridine and 40-15 weight % styrene. These copolymers are commercially available or may be produced by conventional techniques well known in the art. Other copolymers useful in the present invention include copolymers of 2-vinylpyridine and isoprene, butadiene, or acrylate.

Preferred novel polymers useful in the present invention that are made from three or more monomers comprise:
1. from about 50 to about 95 percent by weight of 2-vinylpyridine, and
2. from about 5 to about 50 percent by weight of two or more monomers selected from the group consisting of styrene, isoprene, butadiene, and an alkyl acrylate, wherein the polymer has a glass transition temperature, as measured by differential scanning calorimetry, of from about 50° C. to about 100° C., a water transmission of from 0 to about 29 g.mil/100 inches$^2$/24 hours when measured on a solvent-cast film, and an inherent viscosity of from about 0.3 to about 2.0.

A preferred novel terpolymer suitable for use in the present invention is a novel 2-vinylpyridine/styrene/acrylate or olefin terpolymer comprising from about 50 to about 95 percent by weight of 2-vinylpyridine, preferred is about 65 to about 85 percent; from about 45 to about 2 percent by weight of styrene, preferred is about 30 to about 5 percent; and from about 3 to about 20 percent by weight, preferred is about 5 to about 15 percent, of a monomer selected from the group consisting of isoprene, butadiene and an alkyl acrylate, said terpolymer having a glass transition temperature (Tg), when measured by differential scanning colorimetry (DSC), of from about 50° C. to about 100° C., preferred is about 70° C. to about 90° C., and a water transmission of less than about 29 g.mil/100 inches$^2$/24 hours, preferred is less than about 20 g.mil/100 inches$^2$/24 hours, when measured on a solvent-cast film, and an inherent viscosity (I.V.) about 0.3 to about 2.0, preferred is about 0.8 to about 1.7.

Tg by DSC can be measured by using the procedure disclosed by John Mitchell and Jen Chiu, Anal. Chem. Annual Review, 43,267R (1971); M. J. O'Neill and R. L. Fyans, "Design of Differential Scanning Calorimeters and the Performance of a New System," paper presented at the Eastern Analytical Symposium, New York City, November, 1971.

The inherent viscosities (I.V.) are determined according to ASTM D2857-70 procedure in a Wagner Viscometer of Lab Glass Inc., of Vineland, N.J., having an 0.4 mm capillary and a 1 ml bulb, using a polymer concentration of 0.25% by weight in dimethylforamide solvent. The procedure comprises dissolving the sample at 25° C., and measuring the time of flow at 25° C. The I.V. $\{\eta\}$ is calculated from the equation

$$\{\eta\}^{25°\,C.}_{0.25\%} = \frac{\ln \frac{l_s}{l_o}}{C}$$

wherein:
- {η} = Inherent viscosity at 25° C. at a polymer concentration of 0.5 g/100 mL of solvent;
- ln = Natural logarithm;
- $t_s$ = Sample flow time;
- $t_o$ = Solvent-blank flow time; and
- C = Concentration of polymer in grams per 100 mL of solvent = 0.25.

Water transmission can be determined by the methodology disclosed in ASTM Method F372.

When the novel polymers made from three or more monomers as disclosed herein are used as the polymeric material in the coatings of this invention, the Tg of the composition will be low enough so that the presence of a hydrophobic substance is no longer required. Therefore the present invention also encompasses binary coating compositions and pellets made therefrom which comprises such polymers made from three or more monomers as described hereinbefore and from about 186 to about 485 percent, based on the weight of polymer, of a physiologically acceptable flake material dispersed in said polymeric material, preferably from about 186 to about 400 percent of said flake material.

The acrylate residues of the polymers made from three or more monomers useful in the coatings and pellets of the present invention are derived from an acrylate monomer having the formula wherein R' is H or methyl and R" is a straight, branched or cyclic alkyl group of 1 to 20 carbon atoms. Preferred alkyl groups have 6 to 20 carbon atoms such as n-lauryl, 2-ethylhexyl, cyclohexyl, and iso-octyl. It is preferred that R' is H. Preferred acrylate monomers are n-lauryl acrylate, 2-ethylhexyl acrylate, cyclohexyl acrylate and iso-octyl acrylate.

All of the monomers used to prepare the novel polymers made from three or more monomers (e.g., the preferred 2-vinylpyridine/styrene/acrylate or olefin terpolymer) are well known in the art and can be prepared by well known techniques. Polymers useful in the coatings and pellets of the present invention can be prepared by well known polymerization techniques such as solution or emulsion polymerization (see, for example, U.S. Pat. No. 4,593,082). For example, three respective monomers in the desired proportions, with or without any desired additive, are placed in a reaction vessel in the presence of water and mixed with an emulsifier to form an emulsion. The emulsion is swept with an inert gas such as nitrogen or argon and heated to about 55° C. A polymerization initiator, such as sodium persulfate, is then added to the emulsion and said monomers are allowed to polymerize for a sufficient time to result in the desired terpolymer. After the terpolymer is formed, the temperature is typically adjusted to about 40° C. and a suitable acid such as acetic acid is added to precipitate the terpolymer product. The terpolymer can then optionally be digested, for example, with heat, to obtain better-defined particles. The terpolymer can then be purified using standard procedures known in the art. The terpolymer can then be dissolved in a suitable solvent such as a mixture of 85% acetone and 15% methanol by weight.

Hydrophobic Material

Hydrophobic materials which are physiologically acceptable and have the correct degree of compatability with the polymer are commercially available. It is important that the polymer and hydrophobic substance have a degree of compatability to permit the film to remain intact in the rumen environment, but to permit permeation of the abomasal fluid to the core while the pellet is in the abomasum.

A class of hydrophobic materials of value are fatty acids containing from 10 to 32 carbon atoms such as lauric, oleic, stearic, palmitic and linoleic. These substances are well known to be water insoluble due to the long hydrocarbon radical but to react to water due to the polar nature of the carboxyl group. In the selected basic amino group-containing polymers, the carboxyl group of the fatty acid is able to react with the basic nitrogen group to form a weak salt-type linkage. This attachment to the polymer serves to cause the fatty acid to be fixed in the polymer matrix. The hydrophobic hydrocarbon chain of the fatty acid tends to render the matrix water resistant and thereby decreases swelling of the otherwise water suseptible polar film. Both the interior of the matrix film and the surface is now water resistant in aqueous environments at pH above about 5.0. However, at pH values below pH 4.5 and especially below about pH 3.5 the affinity of the basic nitrogen group for water and the hydrogen ion overcomes the increased water resistance. The film reacts with the acid environment and loses barrier properties sufficient to allow the core material to escape to the environment.

Polyfunctional carboxlyic acids may be derived from natural products or obtained by organic synthesis but the ratio of carboxyl group to hydrophobic organic radical should be at least 1 to 10 based on the molecular weight of the organic radicals. The hydrophobic substance may be one or more polycarboxylic acids or salts thereof having a ratio of 10 to 22 carbon atoms per carboxyl group and a molecular weight of about 300 to about 1000. Also included in this class of synthesized organic hydrophobic acids are mono and polyfunctional acids containing silicone or fluorinated carbon groups located at least 4 atoms distant along the molecular chain from the position of the carboxyl group or groups. Also, included in the class of hydrophobic substances are the nontoxic multivalent metallic salts of the above acids such as the stearates, oleates, fatty acid diamerates, and palmitates of aluminum and iron and the calcium, magnesium and zinc salts of the higher molecular weight crystalline analogs of the above acids. When the cation is trivalent as for aluminum and ferric ion, the molar ratio of organic acid to metal ion is 2 to 1 or 3 to 1 and the acid can be any monofunctional organic acid having one carboxyl group and at least 10 carbon atoms in the organic radical attached to the carboxyl group. When the metal ion is divalent such as ferrous iron, calcium, magnesium or zinc the organic acid may be monocarboxylic or polycarboxylic and the ratio of metal ion to non-carboxylic carbon atoms is at least 1 to 26. Natural and synthetic waxes and resins added at levels depending on the degree of hydrophobicity and compatibility in the matrix film are of value in the practice of the invention. Waxes and resins are useful that have a molecular weight of from 500 to 2000 and a critical surface tension of less than 31 dynes/cm as determined by the Zisman method described in "Contact Angle Wettability and Adhesion," Advances in Chemistry Series #43; Edited by Robert F. Gould; published by the American Chemical Society; 1963; Chapter 1; and have a solubility in the matrix film of less than 5%. Typical waxes and resins include beeswax, petroleum wax, dammar, hard manila, phenolic resins, rosin and maleated low molecular weight polyhydrocarbons. Also included in the hydrophobic substances are polymers having molecular weights of from 2000 to 10,000, a critical surface tension of less than 31 dynes/cm measured by methods in the reference to Zisman described above. Of particular value are the polymers and copolymers containing silicone groups in the main polymer chain or in a side chain and polymers and copolymers containing fluorinated carbon groups in a side chain. Regardless of the exact nature of the hydrophobic material it must be soluble or colloidally dispersible in the coating solvent when one is used.

It is not desired to be bound by any particular theory or mechanism; however, it is believed that the function of the hydrophobic material as a dispersed phase in the protective polymer layer is as follows:

a. reduces wetting of the coating and therefore initial attach by water,
b. reduces total volume of coating affected by water, and
c. extends the length of permeable pathway the water must travel to core.

Functional Flake Material

In accordance with this invention, a physiologically acceptable flake material is dispersed throughout the polymeric matrix. The flake material is substantially inert with respect to the environment of the rumen.

Suitable inert flake materials include aluminum flake, talc, graphite, ground mica, and combinations thereof. Especially suitable are aluminum flake, talc and combinations thereof. Aluminum flake is produced by ball-milling the aluminum in a liquid medium in the presence of a lubricant such as stearic acid. It is available commercially from Alcan Metal Powders, Division of Alcan Aluminum Corporation. Sizes of the flake are generally less than about 100 microns, preferably about 1–60 microns. Talc particle sizes are generally within the range of 0.5–40 microns. It is sometimes beneficial to subject the hydrophobic material and flake material to ball-milling operations such that they are brought into rubbing contact for several hours, thereby increasing the efficiency of the coating.

Figure 1:
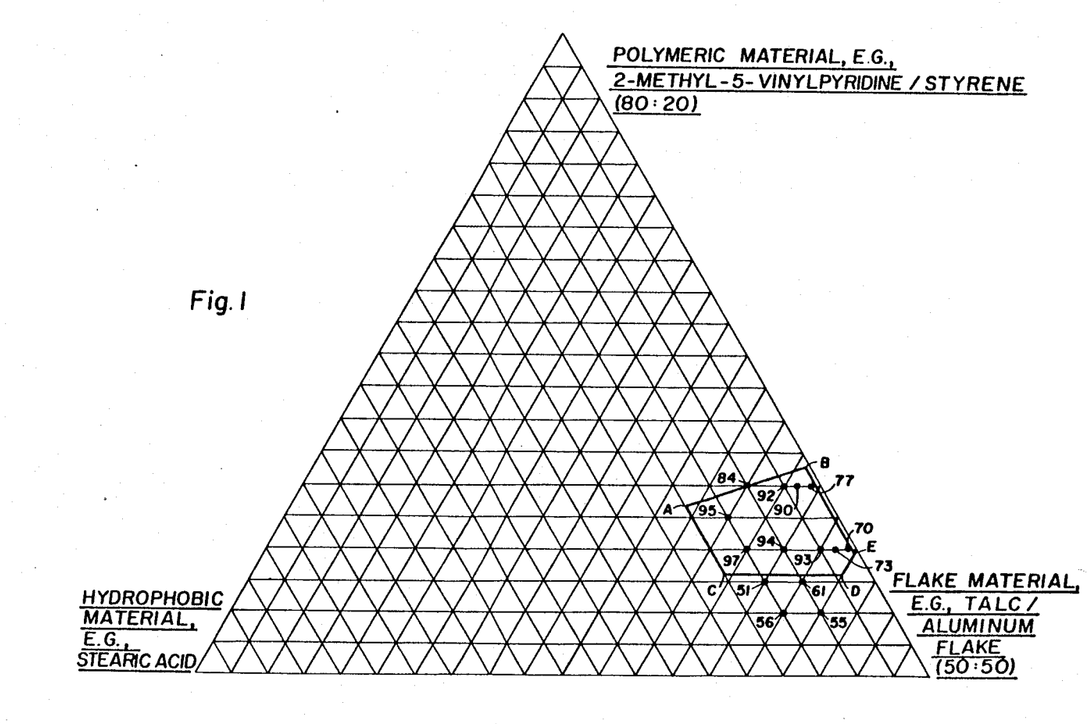

The weight percentages of hydrophobic material and flake material according to this invention are shown in FIG. 1 by the area defined by lines AB, BE, ED, DC and CA. Like AB is shown in greater detail in FIG. 2, where its relationship to U.S. Pat. No. 4,181,708 is also shown. The boundary of the disclosure of '708 is illustrated by broken line FG containing point H, which represents the specific disclosure of the '708 patent closest to applicants' present invention. Like AB is defined as follows:

1. based on percent hydrophobic material, 20% at A and 0.5% at B;
2. based on polymeric material and flake material, straight, parallel, and juxtaposed to line FG. By "Juxtaposed" it is meant spaced from line FG an infinitesimal, or every small, distance but a distance sufficiently large that points on line AB are not graphically equivalent to points on line FG.

The coordinates for points A, B, C, D, E, F, G and H are given in the following table.

| | Coordinates | | |
|---|---|---|---|
| | % Polymeric Material | % Hydrophobic Material | % Flake Material |
| F | 28.09 | 14.05 | 57.87 |
| G | 32.47 | 0.65 | 66.89 |
| H | 31.5 | 3.5 | 65 |
| A | (see below) | 20 | (see below) |
| B | (see below) | 0.5 | (see below) |
| C | 16.5 | 20 | 63.5 |
| D | 16.5 | 3.5 | 80 |
| E | 19.5 | 0.5 | 80 |

Within the definition given above for line AB, suitable coordinates for points A and B are as follows:

| | % Polymeric Material | % Hydrophobic Material | % Flake Material |
|---|---|---|---|
| A | 26 | 20 | 54 |
| A$^1$ | 25.5 | 20 | 54.5 |
| B | 32.4 | .5 | 67.1 |
| B$^1$ | 32 | .5 | 67.5 |

Figure 2:
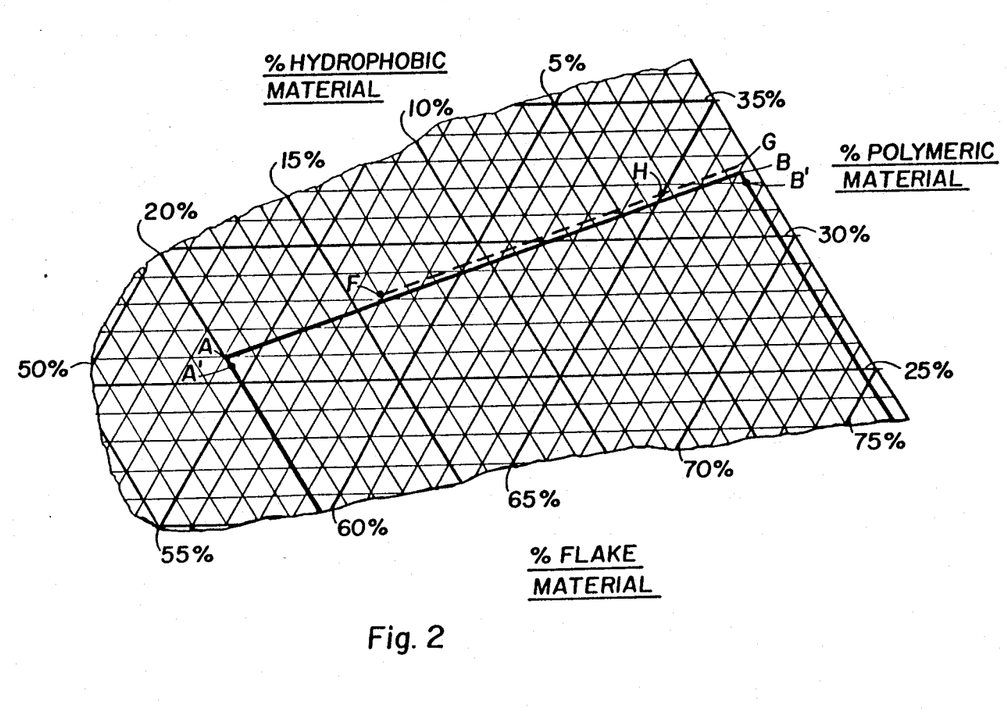

The boundary of the area disclosed by Dannelly '708 closest to the claimed invention is shown at line FG in FIG. 2.

The '708 patent discloses hydrophobic material in amounts ranging from about 2% to about 50%, based on the weight of the polymeric material and flake material in amounts of about 10% to about 206%, based on the weight of polymeric material. These amounts are represented by the following, considering one unit of polymeric material:

| | Case I | Case II | Case III | Case IV |
|---|---|---|---|---|
| Polymeric Material | 1 | 1 | 1 | 1 |
| Hydrophobic Material | 0.02 | 0.02 | 0.5 | 0.5 |
| Flake Material | 0.10 | 2.06 | 0.10 | 2.06 |
| Total | 1.12 | 3.08 | 1.60 | 3.56 |

Converting to percentages based on composition weight rather than polymeric weight, the following percentages are found:

Percentages in Case I:

Polymeric Material $\frac{1}{1.12} = 89.29\%$

Hydrophobic Material $\frac{0.02}{1.12} = 1.78\%$

Flake Material $\frac{0.10}{1.12} = 8.93\%$

Percentages in Case II:

Polymeric Material $\frac{1}{3.08} = 32.47\%$

Hydrophobic Material $\frac{0.02}{3.08} = 0.65\%$

Flake Material $\frac{2.06}{3.08} = 66.88\%$

Percentages in Case III:

Polymeric Material $\frac{1}{1.6} = 62.50\%$

-continued

Hydrophobic Material $\frac{0.5}{1.6} = 31.25\%$

Flake Material $\frac{0.1}{1.6} = 6.25\%$

Percentages in Case IV:

Polymeric Material $\frac{1}{3.56} = 28.09\%$

Hydrophobic Material $\frac{0.5}{3.56} = 14.05\%$

Flake Material $\frac{2.06}{3.56} = 57.87\%$

Obviously Cases II and IV, because of their high contents of flake material, represents the points on the graph closest to the area claimed by applicant. These points are F and G respectively on the graph. Point H illustrates the specific disclosure of the '708 patent in Example 14. Cases I and III represent points far removed from the present invention.

In all situations, the amounts of flake material in the coatings of this invention is greater than about 200%, based on the weight of polymeric material; a preferred amount of flake material is greater than 206% and less than about 380%, based on the weight of polymeric material. In all situations, the amount of hydrophobic substance is between 1.5% and 121%, based on the weight of polymeric material; a preferred amount is between about 5% and about 80% based on the weight of polymeric material.

The Tg values of the coating compositions of the invention is not more than about 60° C., preferred is between about 30° C. and about 60° C. It has been found that when the Tg value of the coating compositions are within the above-noted limit, an unexpected improvement in storage stability (i.e., stability to high humidity and/or heat) is observed. Tg value of the coating compositions can be determined by using thermomechanical analysis (TMA). TMA can be measured on a Perkin-Elmer Model TMS-2 thermomechanical analyzer.

The coating compositions of the present invention have an amount of flake material that is higher than that amount disclosed in the prior art. This increased amount of flake material (i.e., greater than about 200%) contributes to better rumen-protection of the coatings and pellets of the invention and also contributed to better storage stability of the coating and pellets of the invention.

In addition, use of the novel polymers made from three or more monomers described herein as the polymeric material contribute to achieving the lower Tg values of the coatings of the invention.

The coatings of this invention can optionally contain a plasticizer which also can contribute to achieving the lower Tg values of the coatings of the invention. One or more plasticizers are present in an amount of from 0% to about 25%, based on the weight of polymeric material; preferred is from about 5% to about 25%. Typical plasticizers include, but are not limited to, fatty acids, esters of fatty acids, salts of fatty acids, esters of glycols, and polyglycols. Specific examples include triacetin, triethyl citrate, dimethyl adipate, and the like.

The pellets of the present invention preferably have postrumen release of core material of greater than 85%, more preferably greater than 90%. In addition, the pellets of this invention typically exhibit greater than 80% protection, preferably greater than 90%, when stored for 120 hours at 100 relative humidity and ambient temperature.

In the practice of this invention, the polymeric material may conveniently be dissolved in a suitable solvent which would be physiologically acceptable in the event there are residues upon evaporation of the solvent, as hereinbefore described. The hydrophobic substance and flake material are blended in the solution, wherein the polymeric substance is a continuous matrix and the additives are dispersed therein. The coating solution may be applied by various well known means such as, for example, brushing, dipping, spraying, fluidized bed, etc.

The examples which follow are submitted for a better understanding of the invention, but should not be construed as a limitation thereon.

EXAMPLE I

Rumen Studies

While the following examples of Example 1 are based on in vitro tests, the in vitro experiments simulate conditions existing in ruminants thereby permitting the study of coated pellets without the use of live animals. It has been determined by actual in vivo tests using certain coating compositions that the testing of pellets in aqueous media simulating the environmental conditions of the rumen and abomasum with respect to temperature, pH, etc., provide reliable data concerning the protection offered by the coatings in the rumen, and releasability of the coatings in the abomasum. Nutrients such as amino acids and proteins which may be used in the core material are known to be beneficial to ruminants when positioned in the intestinal tract downstream from the rumen.

Generally, pellets are prepared from the nutrients indicated to a size of between about 8 and 12 sieve size. The nutrients are mixed with conventional additives such as microcrystalline cellulose, binders, inert consistency adjusting substances such as water, etc. The pellets are formed by a conventional pelletizer, dried, sieved, and coated using a coater as described herein. Upon application of the coating to the pellets, they are tested for resistance to pH conditions resembling those of the rumen and abomasum by agitating in buffer solutions of pH 2.9 for 0.5 hours and 5.4 for 24 hours. Recovery and protection figures cited for active core ingredients herein contain in them all materials of the original coated pellet that are not completely dissolved in the pH 2.9 buffer, including any undissolved active ingredient in the original core. For the sake of simplicity abbreviations are used in the examples as follows:

2M5VP—2-methyl-5-vinylpyridine
AN—acrylonitrile
ST—styrene

Cylindrical smooth-edge glucose cores (−8/+12 mesh, U.S. standard mesh size) which consist of 90% glucose and 10% microcrystalline cellulose are used in all experiments. In the process of preparing glucose cores, glucose powder and microcrystalline cellulose are mixed thoroughly in a Hobart mixer-extruder; water is then added slowly to wet the dry solid mix until an extrudable dope was formed. The moisture content of the final dope is about 18%. The dope is extruded from the mixer-extruder through a die with 2-mm diameter holes and chopped with a rotating knife into small cylinders with a length/diameter ratio approximately equal to one. Wet cores are tumbled to smooth the rough edges, and then dried in an oven at 60° C. Dry cores are screened to yield uniform size cores for all coating experiments.

In preparing the coating dopes, a mixture of copoly(2M5VP/ST 80:20) (I.V.=1.30), stearic acid, and talc/aluminum flake (1:1 w/w) are mixed in acetone to make a series of coating dopes containing 5% solids. The exact coating compositions are shown as dots in the tricompositional diagram in FIG. 1. The coordinates represent percentage of total composition weight of the polymeric material, hydrophobic material and flake material. Glucose cores are coated with the coatings dopes to desired coating levels using an air-suspension coater under the same operating conditions.

Rumen-protection and abomasal release are measured by extracting coated pellets in pH 5.4 buffer for 24 hours and pH 2.9 buffer for one hour respectively. Protection values are obtained for pellets with 6, 12, and 18% coating levels for each coating composition. The protection value at 15% coating weight for each coating composition is determined and indicated in at the respective coating compositions in FIG. 1. For example, the rumen protection value of pellets coated with 20/70/10 (2M5VP/ST)/(Talc/Al)/stearic acid is 94%. All the coating compositions shown in Table 1 have abomosal release in excess of 90%.

To illustrate the effect of coating amino acids with certain coating compositions, lysine and methionine are coated with compositions described as follows:

|  | Lysine |  | Methionine |  |
|---|---|---|---|---|
| Polymer | 2M5VP/ST) 80:20%) | 31.5% | 2M5VP/ST 80:20% | 31.5% |
| Hydrophobic Material | Stearic Acid | 5.0% | Stearic Acid | 3.5% |
| Flake Material | Aluminum Flake | 63.5% | Aluminum Flake | 26.0% |
|  |  |  | Talc | 39.0% |
| Coating Weight, Based on Weight of Coated Pellets | 18% |  | 14% |  |

The coated pellets are fed to calves for 140 days. The actual doses of methionine and lysine were each between about 0.05% and about 0.3%, based on percent of diet on a dry matter basis. Over the entire trial, average daily weight gain increased about 6% when compared to the control groups which were fed no lysine and methionine, indicating rumen protection and delivery postruminally of the amino acids. Thus, the in vitro test results indicating effectiveness of the coatings are confirmed in vivo.

The coating compositions disclosed in this invention are also useful for other bioactive materials, particularly highly water-soluble amino acids such as lysine, carbohydrates, vitamins, antibiotics, hormones, and other pharmaceuticals. In general, a highly water-soluble active ingredient is much more difficult to protect less water-soluble bioactive compound and a successful rumen-stable coating for highly water-soluble materials is obviously useful for materials of low water solubility so that the coating compositions in this invention may be viewed as an universal coating which is independent of the solubility of the core material.

Unless otherwise specified, all parts, percentages, ratios, etc., are by weight. Molecular weights are given as weight averages.

Unless otherwise specified, the inherent viscosity (I.V.) of the polymers is determined at 25° C., using 0.25 gram polymer per 100 mL of a solvent composed of dimethylformamide.

EXAMPLE II

1. This example illustrates the instability of a ternary rumen-stable coating formulation when subjected to 100% relative humidity to simulate feed contact for up to five days.

In an air-suspension coater, 200 grams of lysine.HCl and methionine containing pellets were coated with a rumen-stable coating formulation consisting of 31.5% 2-vinylpyridine/styrene (65/35) copolymer, 63.5% talc, and 5.0% stearic acid to a coating level of ~16.5% by weight. A sample of coated pellets (one gram) was extracted in 50 mL of pH 5.4 buffer solution for 24 hours to determined rumen stability. No sigificant amount of lysine.HCl or methionine was detected in the extract. A sample of coated pellets was extracted in pH 2.9 buffer for 45 minutes followed by pH 7.0 buffer for 2.0 hours to test abomasal release. Analysis of the extracts showed greater than 95% release of the payload. Coated samples (one gram) of the pellets were placed in a closed chamber at 100% relative himidity at room temperature (22° C.) for 24, 48, and 72 hours. Following removal from the chamber, the coated samples were extracted in 50 mL of pH 5.4 buffer solution for 24 hours to determine the effect of 100% relative humidity on the rumen stability. The effect of exposure to 100% relative humidity on the rumen stability (percent protection) is shown in the following table:

| Time in | % Protection | |
|---|---|---|
| 100% RH (Hours) | Lysine.HCl | Methionine |
| 0 | 100 | 100 |
| 24 | 99 | 100 |
| 48 | 84 | 96 |
| 72 | 42 | 74 |

A very significant drop of lysine.HCl protection was observed after 72 hours exposure at 100% RH. The glass transition temperature (Tg) of the coating composition measured by thermal mechanical analysis (TMA) was about 88° C.

2. This example illustrates the use of an optimized ternary rumen-stable coating formulation to achieve improved feed stability of lysine.HCl and methionine containing pellets.

Using the same conditions as in Example II, 1, lysine.HCl and methionine containing pellets were coated with a rumen-stable coating formulation consisting of 20% 2-vinylpyridine/styrene (65/35) copolymer, 60% talc, and 20% stearic acid to a coating level of 16.5% by weight. Coated samples were extracted in pH 5.4 buffer solution for 24 hours to determine rumen stability. No significant amount of lysine.HCl or methionine was detected in the extract. A sample of coated pellets was extracted in pH 2.9 buffer for 45 minutes followed by pH 7.0 buffer for 2.0 hours to test abomasal release. Analysis of the extracts showed greater than 95% release of the payload. Coated pellet samples were placed in a chamber at 100% relative humidity at room temperature (22° C.) for 24, 48, 72, 96, and 120 hours. Following removal from the chamber at 100% relative humidity, the coated samples were extracted in pH 5.4 buffer solution for 24 hours to determine rumen stability. The effect of 100% relative humidity on rumen stability (percent protection) is shown in the following table:

| Time in | % Protection | |
| 100% RH (Hours) | Lysine.HCl | Methionine |
| --- | --- | --- |
| 0 | 100 | 100 |
| 24 | 100 | 99 |
| 48 | 98 | 98 |
| 72 | 98 | 99 |
| 96 | 96 | 97 |
| 120 | 90 | 93 |

Coated pellet samples from Example 2 show a very significant increase in protection after 72 hours exposure to 100% relative humidity over that of samples from Example II, 1, a 56% improvement. The Tg of the coating composition measured by TMA was about 50° C.

3. This example illustrates the incorporation of a plasticizer, triacetin, into a ternary composition to produce a quanternary composition which exhibits much improved feed stability characteristics compared to the ternary composition.

Using the same conditions as in Example II, lysine.HCl an methionine containing pellets were coated with a rumen-stable coating composition comprised of essentially the same composition as given in Example II, 1 [(31.5% 2-vinylpyridine/styrene (65/35), 63.5% talc, and 5.0% stearic acid] and an additional amount of 20% triacetin by weight of the 2-vinyl-pyridine/styrene. Coating weight applied to the pellets was 16.5% by weight. Coated pellet samples were extracted in pH 5.4 buffer solution for 24 hours to determine rumen stability. No significant amount of lysine.HCl or methionine was detected in the extract. A sample of coated pellets was extracted in pH 2.9 buffer for 45 minutes followed by pH 7.0 buffer for 2.0 hours to test abomasal release. Analysis of the extracts showed greater than 95% release of the payload. Coated pellets samples were placed in a chamber at 100% relative humidity at room temperature for 24, 48, 72, 96, and 120 hours. Following removal from the 100% relative humidity, the coated pellet samples were extracted in pH 5.4 buffer solution for 24 hours to determine rumen stability. The effect of 100% relative humidity on rumen stability is shown in the following table:

| Time in | % Protection | |
| 100% RH (Hours) | Lysine.HCl | Methionine |
| --- | --- | --- |
| 0 | 100 | 100 |
| 24 | 100 | 100 |
| 48 | 100 | 100 |
| 72 | 100 | 99 |
| 96 | 98 | 99 |
| 120 | 99 | 99 |

The glass transition temperature of the coating composition measured by TMA was about 55° C.

4. This example illustrates the incorporation of a selected plasticizer, triethyl citrate, into a ternary composition to produce a quaternary composition which exhibits much improved feed stability characteristics compared to the ternary composition.

Using the same conditions as in Example II, 2, lysine.HCl and methionine containing pellets were coated with a rumen-stable coating composition comprised of essentially the same composition as given in Example II, 1 [31.5% 2-vinylpyridine/styrene (65/35), 63.5% talc, and 5.0% stearic acid] and an additional amount of 15% triethyl citrate by weight of the 2-vinylpyridine/styrene. Coating weight applied to the pellets was 16.5% by weight. Coated pellet samples were extracted in pH 5.4 buffer solution for 24 hours to determine rumen stability. No significant amount of lysine.HCl or methionine ws detected in the extract. A sample of coated pellets was extracted in pH 2.9 buffer for 45 minutes, 2.0 hours to test abomasal release. Analysis of the extracts showed greater than 95% release of the payload. Coated pellet samples were placed in a chamber at 100% relative humidity at room temperature for 24, 48, 72, 96, and 120 hours. Following removal from 100% relative humidity, the coated pellet samples were extracted in pH 5.4 buffer solution for 24 hours. The effect of 100% relative humidity on rumen stability is shown in the following table:

| Time in | % Protection | |
| 100% RH (Hours) | Lysine.HCl | Methionine |
| --- | --- | --- |
| 0 | 100 | 99 |
| 24 | 99 | 99 |
| 48 | 100 | 99 |
| 72 | 100 | 99 |
| 96 | 99 | 99 |
| 120 | 99 | 99 |

The Tg of coating composition measured by TMA was about 45° C.

5. This example illustrates the use of a ternary coating composition containing an acid-sensitive terpolymer to improve feed stability characteristics.

Using the same conditions as in Example II, 2, lysine.HCl and methionine containing pellets were coated with a rumen-stable composition comprised of 31.5% 2-vinylpyridine/styrene/lauryl acrylate (65/25/10), 63.5% talc, and 5.0% stearic acid. Coating weight applied to the pellets was 15% by weight. Coated pellet samples were extracted in pH 5.4 buffer solution for 24 hours to determine rumen stability. No significant amount of lysine.HCl or methionine was detected in the extract. A sample of coated pellets was extracted in pH 2.9 buffer for 45 minutes followed by pH 7.0 buffer for 2.0 hours to test abomasal release. Analysis of the extracts showed greater than 95% release of the payload. Coated pellet samples were placed in a chamber at 100% relative humidity at room temperature for 24, 48, 72, 96, and 120 hours. Following removal from the chamber at 100% relative humidity, the coated pellet samples were extracted in pH 5.4 buffer solution for 24 hours. The effect of 100% relative humidity exposure on the rumen stability is shown in the following table:

| Time in | % Protection | |
| 100% RH (Hours) | Lysine.HCl | Methionine |
| --- | --- | --- |
| 0 | 100 | 100 |
| 24 | 98 | 99 |
| 48 | 100 | 99 |
| 72 | 100 | 99 |
| 96 | 100 | 100 |
| 120 | 100 | 99 |

The Tg of the coating composition measured by TMA was about 52° C.

6. This example illustrates the use of a binary coating composition containing an acid-sensitive terpolymer to improve feed stability characteristics.

Using the same conditions as in Example II, 2, lysine.HCl and methionine containing pellets were coated with a rumen-stable coating composition comprised of 28% 2-vinylpyridine/styrene/lauryl acrylate (65/25/10) and 72% talc. The coating weight applied to the pellets was 16.5% by weight. Coated pellet samples were extracted in pH 5.4 buffer solution for 24 hours to determine rumen stability. No significant amount of lysine.HCl or methionine was detected in the extract. Coated pellet samples were also extracted in pH 2.9 buffer for 45 minutes followed by pH 7.0 buffer for 2.0 hours. Analysis of the extracts showed greater than 95% release of the payload. Coated pellet samples were placed in a chamber at 100% relative humidity at room temperature for 24, 48, 72, 96, and 120 hours. Following removal from the chamber at 100% relative humidity, the coated pellet samples were extracted in pH 5.4 buffer solution for 24 hours. The effect of 100% relative humidity exposure on the rumen stability is shown in the following table:

| Time in 100% RH (Hours) | % Protection Lysine.HCl | Methionine |
|---|---|---|
| 0 | 100 | 100 |
| 24 | 100 | 99 |
| 48 | 99 | 99 |
| 72 | 90 | 98 |
| 96 | 76 | 95 |
| 120 | 82 | 96 |

The Tg of the coating composition measured by TMA was about 52° C.

7. This example illustrates the use of a binary coating composition containing an acid-sensitive terpolymer to improve feed stability characteristics.

Using the same conditions as in Example II, 2, lysine.HCl and methionine containing pellets were coated with a rumen-stable coating composition comprised of 56% 2-vinylpyridine/styrene/lauryl acrylate (65/25/10) and 44% talc. The coating weight applied to the pellets was 16.5% by weight. Coated pellet samples were extracted in pH 5.4 buffer solution for 24 hours to determine rumen stability. No significant amount of lysine.HCl or methionine was detected in the extract. Coated pellet samples were also extracted in pH 2.9 buffer for 45 minutes followed by pH 7.0 buffer for 2.0 hours. Analysis of the extract showed greater than 95% release of the payload. Coated pellet samples were placed in a chamber at 100% relative humidity at room temperature for 24, 48, 72, 96, and 120 hours. Following removal from the chamber at 100% relative humidity, the coated pellet samples were extracted in pH 5.4 buffer solution for 24 hours. The effect of 100% relatively humidity exposure on the rumen stability is shown in the following table:

| Time in 100% RH (Hours) | % Protection Lysine.HCl | Methionine |
|---|---|---|
| 0 | 100 | 100 |
| 24 | 86 | 97 |
| 48 | 86 | 97 |
| 72 | 85 | 97 |
| 96 | 85 | 98 |

The Tg of the coating composition measured by TMA was about 52° C.

8. This example illustrates the stability of a ternary rumen-stable coating formulation when subjected to 100% relative humidity to simulate feed contact. In an air-suspension coater, 180 grams of pellets containing lysine.HCl and methionine were coated with a rumen-stable coating formulation consisting of 31.5% 2-vinylpyridine/styrene (80/20) copolymer, 63.5% talc, and 5.0% stearic acid to a coating level of 15.3% by weight. A sample of coated pellets (1.0 gram) was extracted in 50 mL of pH 5.4 buffer solution of 39° C. for 24 hours to determine rumen stability. No significant amount of lysine.HCl was detected in the extract. Coated samples (1.0 gram) of the pellets were placed in a closed chamber at 100% relative humidity at room temperature (22° C.) for 24, 48, an 72 hours. Following removal from the chamber, the coated samples were extracted in 50 mL of pH 5.4 buffer solution at 39° C. for 24 hours to determine the effect of 100% relative humidity on the rumen stability. The effect of the 100% relative humidity on the rumen stability (percent protection) is shown in the following table:

| Time in 100% RH (Hours) | % Protection Lysine.HCl | Methionine |
|---|---|---|
| 0 | 98 | 100 |
| 24 | 94 | 100 |
| 48 | 68 | 91 |
| 72 | 10 | 66 |

The Tg of the coating composition measured by TMA was about 62° C.

9. This example illustrates the incorporation of a plasticizer into a ternary rumen-stable coating to achieve improved feed stability of pellets containing lysine.HCl and methionine. Using the same conditions as in Example II, 8, pellets containing lysine.HCl and methionine were coated with a rumen-stable coating formulation consisting of 31.5% 2-vinylpyridine/styrene (80/20) copolymer, 63.5% talc, and 5.0% oleic acid to a coating level of 15.3% by weight. A sample of coated pellets (1.0 gram) was extracted in 50 mL of pH 5.4 buffer solution at 39° C. for 24 hours to determine rumen stability. No significant amount of lysine.HCl was detected in the extract. Coated samples (1.0 gram) of the pellets were placed in a closed chamber at 100% relative humidity at room temperature (22° C.) for 24, 48, and 72 hours. Following removal from the chamber, the coated samples were extracted in 50 mL of pH 5.4 buffer solution at 39° C. for 24 hours to determine the effect of 100% relative humidity on the rumen stability. The effect of the 100% relative humidity on the rumen stability (percent protection) is shown in the following table:

| Time in 100% RH (Hours) | % Protection Lysine.HCl | Methionine |
|---|---|---|
| 0 | 96 | 100 |
| 24 | 97 | 100 |

| Time in | % Protection | |
|---|---|---|
| 100% RH (Hours) | Lysine.HCl | Methionine |
| 48 | 94 | 100 |
| 72 | 84 | 98 |

Coated pellet samples from Example 9 show a large increase in stability to 100% relative humidity over that of samples in Example 8.

The Tg of the coating composition measured by TMA was about 56° C.

10. This example illustrates the incorporation of a plasticizer into a ternary composition to produce a quaternary composition which exhibits much improved feed stability characteristics compared to the ternary composition. Using the same conditions as in Example II, 2, pellets containing lysine.HCl and methionine were coated with a rumen-stable coating formulation consisting of 30.25% 2-vinylpyridine/styrene (80/20) copolymer, 62.25% talc, 3.75% stearic acid, and 3.75% oleic acid to a coating level of 15.3% by weight. A sample of coated pellets (1.0 gram) was extracted in 50 mL of pH 5.4 buffer solution at 39° C. for 24 hours to determine rumen stability. No significant amount of lysine.HCl was detected in the extract. Coated samples (1.0 gram) of the pellets were placed in a closed chamber at 100% relative humidity at room temperature (22° C.) for 24, 48, and 72 hours. Following removal from the chamber the coated samples were extracted in 50 mL of pH 5.4 buffer solution at 39° C. for 24 hours to determine the effect of 100% relative humidity on the rumen stability. The effect of the 100% relative humidity on the rumen stability. The effect of the 100% relative humdity on the rumen stability (percent protection) is shown in the following table:

| Time in | % Protection | |
|---|---|---|
| 100% RH (Hours) | Lysine.HCl | Methionine |
| 0 | 95 | 99 |
| 24 | 94 | 100 |
| 48 | 94 | 100 |
| 72 | 91 | 99 |

The Tg of the coating composition measured by TMA was about 50° C.

11. This example illustrates the stability of rumen-stable coatings in a moist feed environment. Ten grams of coated pellets were mixed with approximately 200 g of a typical dairy feed ration. The feed ration contained 1,342 g of corn silage, 37 g corn mean, 24.8 g soybean meal, and 3.8 g of minerals. The moisture content of the feed was 43.2% and the pH of the feed was 5.1. Pellet samples were mixed into the feed at room temperature for 24 to 48 hours. One gram of pellets was removed from the feed. Following removal from the feed, the coated samples were extracted in 50 mL of pH 5.4 buffer solution for 24 hours to determine the effect of feed content on rumen stability. The effect of exposure to feed on rumen stability (percent protection) is shown in the following table;

| Sample | Tg | % Protection 24 Hours | | % Protection 48 Hours | |
|---|---|---|---|---|---|
| | | Lysine | Methionine | Lysine | Methionine |
| Example II, 1 | 88° C. | 54 | 97 | 28 | 98 |
| Example II, 3 | 55° C. | 100 | 99 | 97 | 99 |

EXAMPLE III

1. 65/25/10 Poly(2-vinylpyridine-co-styrene-co-lauryl acrylate)

To a 3,000-mL, three-neck flask equipped with condenser, mechanical stirrer, thermometer and a heating mantle are charged 2-vinylpyridine (260 g, 2.473 mol), styrene (100 g, 0.962 mol), lauryl acrylate (40 g, 0.177 mol), premixed sodium oleate (12 g, 0.039 mol) in water (240 mL) 50% sodium hydroxide (20 g, 0.250 mol) and water (960 mL). The contents are swept with nitrogen and heated to 55° C. Sodium persulfate (3.6 g, 0.015 mol) is added and the reaction is agitated at 55° C. with a heating mantle for 18 hours under nitrogen to give a white milky emulsion.

The batch temperature is adjusted to 40° C. and acetic acid (16 g, 0.267 mol) in water (960 mL) is added over 15 minutes to precipitate the product while allowing the batch temperature to drift downward. During this time, the milky emulsion breaks into a thick white paste which upon heating to 60° C. over 1 hour turns into a thinner slurry with better-defined particles. The batch is further digested at 60° C. for 15 minutes, cooled to room temperature and filtered. The cake is washed with water (4,000 mL) and then pulled with vacuum on a Büchner funnel. After drying in a 55° C. oven, a total of 400.7 g (100% yield) of white powder is obtained. The dried polymer has a composition of 67 mol % 2-vinylpyridine: 27 mol % styrene: 6 mol % lauryl acrylate by nuclear magnetic resonance (NMR) spectroscopy, a Tg of 88° C. by differential scanning calorimetry (DSC), an I.V. of 1.075 when determined in N,N-dimethylformamide (DMF) and a water transmission rate of 16.5 g.mil/100 in.$^2$/24 hours when measured on a solvent-cast film. This solvent cast film is flexible and the polymer is suitable for coating amino acids when used in combination with standard filler and additives as demonstrated by the results in Examples II, 5; II, 6; and II, 7.

2. 65/25/10 Poly(2-vinylpyridine-co-styrene-co-2-ethylhexyl acrylate)

The procedure as described in Example III, 1 is followed except that 2-ethylhexyl acrylate (40 g, 0.217 mol) is used in place of lauryl acrylate to give 398.7 g (99.7% yield) of dried polymer in the form of a white powder. The dried polymer has a composition of 66 mol % 2-vinylpyridine: 27 mol % styrene: 7 mol % 2-ethylhexyl acrylate by NMR, a Tg of 83° C. by DSC, an I.V. of 1.169 in DMF and a water transmission rate of 16.5 g.mil/100 in.$^2$/24 hours when measured on a solvent-cast film. This solvent-cast film is flexible and the polymer is suitable for coating amino acids when used in combination with standard fillers and additives.

3. 65/35 Poly(2-vinylpyridine-co-styrene)

A mixture of 2-vinylpyridine (650 g, 6.190 mol) and styrene (350 g, 3.365 mol) is washed twice with 5%

NaOH (each 320 mL) then twice with water (each 640 mL) in a separatory funnel to remove inhibitors. The prewashed 65/35 2-vinylpyridine/styrene, premixed sodium oleate (33 g 0.108 mol) in water (660 mL), 50% NaOH (30.0 g, 0.375 mol) and water (5,340 mL) are charged into a 10-liter, three-neck flask equipped with mechanical stirrer, condenser and thermometer. The contents are purged with nitrogen and sodium persulfate (5.0 g, 0.021 mol) is added. The reaction is heated to 55° C. with a water bath under nitrogen and then maintained at 55° C. for 8 hours to give a milky emulsion. The batch is divided into four equal parts, of which one is worked up as follows. An emulsion equivalent to 250 g polymer from above is added to an agitated solution of sodium chloride (48 g) and distilled water (600 mL) in a 5,000-mL three-neck flask equipped with a mechanical stirrer and a condenser. The emulsion breaks into a thick cottage-cheese like slurry. The reaction mixture is heated to and maintained at 80° C. for 15 minutes. The batch is cooled to room temperature over 2-4 hours. The product is filtered on a Büchner funnel with house vacuum and washed with distilled water (6,000 mL). The wet cake is pulled on the funnel and dried in a 55° C. oven to give 250.0 g white powder (100% yield). The dried polymer has a composition of 63 mol percent 2-vinylpyridine: 37 mol percent styrene by NMR, a Tg of 105° C. by DSC, an I.V. of 1.169 in dimethylformamide (DMF) and a water transmission rate of 29 g.mil/10 inches$^2$/24 hours when measured on a solvent-cast film. This example represents the unmodified 2-vinylpyridine/styrene copolymer. Films of this polymer are brittle and the coated amino acids are less stable than those coated by the polymer described in Examples III, 1 and III, 2.

The invention has been described in detail with particular reference to preferred embodiments thereof, but it will be understood that variations and modifications can be effected within the spirit and scope of the invention.

We claim:

1. A pellet adapted for oral administration to a ruminant comprising a core material beneficial to the ruminant postruminally, and a coating surrounding said core material which protects the core material in the rumen and releases it postruminally, said coating comprising
   (a) a physiologically acceptable film-forming polymeric material comprising a polymer, or mixture of polymers, said polymeric material having basic amino groups the nitrogen content of which constitutes between about 2% and about 14% by weight of the polymeric material,
   (b) between 1.5% and 121%, based on the weight of polymeric material, of a hydrophobic material dispersed in said polymeric material selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and
   (c) greater than about 200% and up to 485%, based on the weight of said polymeric material, of a physiologically acceptable flake material dispersed in said polymeric material.
said polymeric material in combination with said hydrophobic material being physiologically acceptable and resistant to a pH of greater than about 5 but capable of releasing the core of the pellets at a pH of less than about 3.5, said coating making up about 5% to about 50% of the weight of said pellet, and said coating having a glass transition temperature of not more than about 60° C. as measured by TMA.

2. A pellet according to claim 1 wherein the core comprises a substance having a solubility in water of greater than 60 gm/100 gm water at 25° C.

3. A pellet according to claim 1 wherein the core comprises lysine.

4. A pellet according to claim 1 wherein said coating additionally containing from 0 to about 25%, based on the weight of polymeric material, of a plasticizer.

5. A pellet according to claim 1 wherein the glass transition temperature of said coating is between about 30° C. and about 60° C.

6. A pellet according to claim 1 wherein the amount of Component (b) is between about 5% and about 80%, based on the weight of polymeric material, and the amount of Component (c) is greater than 206% and less than about 380%, based on the weight of polymeric material.

7. A pellet adapted for oral administration to a ruminant comprising a core material beneficial to the ruminant postruminally, and a coating surrounding said core material which protects the core material in the rumen and releases it postruminally, said coating comprising
   (a) a physiologically acceptable film-forming polymeric material comprising a polymer, or mixture of polymers, said polymeric material having basic amino groups the nitrogen content of which constitutes between about 2% and about 14% by weight of the polymeric material,
   (b) between 1.5% and 121%, based on the weight of polymeric material, of a hydrophobic material dispersed in said polymeric material selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and
   (c) greater than about 200% and up to 485%, based on the weight of said polymeric material, of a physiologically acceptable flake material selected from talc, aluminum flake and combinations thereof dispersed in said polymeric material,
said polymeric material in combination with said hydrophobic material being physiologically acceptable and resistant to a pH of greater than about 5 but capable of releasing the core of the pellets at a pH of less than about 3.5, said coating making up about 5% to about 50% of the weight of said pellet, and said coating having a glass transition temperature of not more than about 60° C. as measured by TMA.

8. A pellet according to claim 7 wherein the amount of Component (b) is between about 5% and about 80%, based on the weight of polymeric material, and the amount of Component (c) is greater than 206% and less than about 380%, based on the weight of polymeric material.

9. A pellet adapted for oral administration to a ruminant comprising a core material beneficial to the ruminant postruminally, and a coating surrounding said core material which protects the core material in the rumen and releases it postruminally, said coating comprising
   (a) a physiologically acceptable film-forming polymeric material comprising a polymer, or mixture of polymers, said polymeric material having basic amino groups the nitrogen content of which constitutes between about 2% and about 14% by weight of the polymeric material, (b) between 1.5% and 121%, based on the weight of polymeric material, of a hydrophobic material dispersed in said polymeric material selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and (c) greater than about 200% and up to 485%, based on the weight of said polymeric material, of a physiologically acceptable flake material selected from talc, aluminum flake, graphite, ground mica and combinations thereof dispersed in said polymeric material, said polymeric material in combination with said hydrophobic material being physiologically acceptable and resistant to a pH of greater than about 5 but capable of releasing the core of the pellets at a pH of less than about 3.5, said coating making up about 5% to about 50% of the weight of said pellet, and said coating having a glass transition temperature of not more than about 60° C. as measured by TMA.

10. A pellet according to claim 9 wherein the amount of Component (b) is between about 5% and about 80%, based on the weight of polymeric material, and the amount of Component (c) is greater than 206% and less than about 380%, based on the weight of polymeric material.

11. A composition adapted for use in coating pellets orally administrable to ruminants which protects the core material in the rumen and releases it postruminally, said composition comprising (a) a physiologically acceptable film-forming polymeric material comprising a polymer, or mixture of polymers, said polymeric material having basic amino groups the nitrogen content of which constitutes between about 2% and about 14% by weight of the polymeric material, (b) between 1.5% and 121%, based on the weight of polymeric material, of a hydrophobic material dispersed in said polymeric material selected from the group consisting of axes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and (c) greater than about 200% and up to 485%, based on the weight of said polymeric material, of a physiologically acceptable flake material dispersed in said polymeric material, said polymeric material in combination with said hydrophobic material and flake material being physiologically acceptable and resistant to a pH of greater than about 5 but capable of releasing the core of the pellets at a pH of less than about 3.5, and said composition having a glass transition temperature of not more than about 60C as measured by TMA.

12. A pellet according to claim 11 wherein the amount of Component (b) is between about 5% and about 80%, based on the weight of polymeric material, and the amount of Component (c) is greater than 206% and less than about 380%, based on the weight of polymeric material.

13. A composition according to claim 11 wherein the core comprises a substance having a solubility in water of greater than 60 gm/100 gm water at 25° C.

14. A composition according to claim wherein the core comprises lysine.

15. A composition according to claim 11 wherein said composition additionally contains from about 0 to about 25%, based on the weight of said polymeric material, of a plasticizer.

16. A composition according to claim 11 wherein the glass transition temperature of the composition is between about 30° C. and about 60° C.

17. A composition adapted for use in coating pellets orally administrable to ruminants which protects the core material in the rumen and releases it postruminally, said composition comprising (a) a physiologically acceptable film-forming polymeric material comprising a polymer, or mixture of polymers, said polymeric material having basic amino groups the nitrogen content of which constitutes between about 2% and about 14% by weight of the polymeric material, (b) between 1.5% and 121%, based on the weight of polymeric material, of a hydrophobic material dispersed in said polymeric material selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group, and (c) greater than about 200% and up to 485%, based on the weight of said polymeric material, of a physiologically acceptable flake material selected from talc, aluminum flake and combinations thereof dispersed in said polymeric material, said polymeric material in combination with said hydrophobic material and flake material being physiologically acceptable and resistant to a pH of greater than about 5 but capable of releasing the core of the pellets at a pH of less than about 3.5, and said composition having a glass transition temperature of not more than about 60° C. as measured by TMA.

18. A pellet according to claim 17 wherein the amount of Component (b) is between about 5% and about 80%, based on the weight of polymeric material, and the amount of Component (c) is greater than 206% and less than about 380%, based on the weight of polymeric material.

19. A composition adapted for use in coating pellets orally administrable to ruminants which protects the core material in the rumen and releases it postruminally, said composition comprising (a) a physiologically acceptable film-forming polymeric material comprising a polymer, or mixture of polymers, said polymeric material having basic amino groups the nitrogen content of which constitutes between about 2% and about 14% by weight of the polymeric material, (b) between 1.5% and 121%, based on the weight of polymeric material, of a hydrophobic material dispersed in said polymeric material selected from the group consisting of waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxylic group, and (c) greater than about 200% and up to 485%, based on the weight of said polymeric material, of a physiologically acceptable flake material selected from talc, aluminum flake, graphite, ground mica and combinations thereof dispersed in said polymeric material, said polymeric material in combination with said hydrophobic material and flake material being physiologically acceptable and resistant to a pH of greater than about 5 but capable of releasing the core of the pellets at a pH of less than about 3.5, and said composition having a glass transition temperature of not more than about 60° C. as measured by TMA.

20. A pellet according to claim 19 wherein the amount of Component (b) is between about 5% and about 80%, based on the weight of polymeric material, and the amount of Component (c) is greater than 206% and less than about 380%, based on the weight of polymeric material.

21. A composition adapted for use in coating pellets orally administrable to ruminants which protects the core material in the rumen and releases it postruminally, said composition comprising
(a) a polymer comprising
  (1) from about 50 to about 95 percent by weight of a 2-vinylpyridine residue, and
  (2) from about 5 to about 50 percent by weight of two or more residues of monomers selected from the group consisting of styrene, isoprene, butadiene, and an alkyl acrylate, said polymer having a glass transition temperature (Tg), when measured by differential scanning calorimetry of from about 50° C. to about 100° C. and a water transmission of less than about 29 g.mil/100 inches$^2$/24 hours when measured on a solvent-cast film, and an inherent viscosity (I.V.) about 0.3 to about 2.0, and
(b) from about 186 to about 485 precent, based on the weight of said polymer, of a physiologically acceptable flake material dispersed in said polymer, said polymer in combination with said flake material being physiologically accceptable and resistant to a pH of greater than about 5 but capable of releasing the core of the pellets at a pH of less than about 3.5, and said composition having a glass transition temperature as measured by TMA of not more than about 60° C.

22. A composition according to claim 21 wherein the core comprises lysine.

23. A composition according to claim 21 wherein the glass transition temperature of the composition is between about 30° C. and about 60° C.

24. A composition according to claim 21 wherein said polymer has an acrylate residue derived from an acrylate monomer having the formula wherein R' is H or methyl and R" is a straight, branched or cyclic alkyl group of 1 to 20 carbon atoms.

25. A composition according to claim 24 wherein said acrylate monomer is selected from the group consisting of n-lauryl acrylate, 2-ethylhexyl acrylate, cyclohexyl acrylate, and iso-octyl acrylate.

26. A composition adapted for use in coating pellets orally administrable to ruminants which protects the core material in the rumen and releases it postruminally, said composition comprising
(a) a 2-vinylpyridine/styrene/acrylate or olefin terpolymer comprising
  (1) from about 50 to about 95 percent by weight of 2-vinylpyridine,
  (2) from about 45 to about 2 percent by weight of styrene, and
  (3) from about 3 to about 20 percent by weight of isoprene, butadiene or alkyl acrylate, said terpolymer having a glass transition temperature (Tg), when measured by differential scanning calorimetry of from about 50° C. to about 100° C. and a water transmission of less than about 29 g.mil/100 inches$^2$/24 hours when measured on a sovlent-cast film, and an inherent viscosity (I.V.) about 0.3 to about 2.0, and
(b) from about 200 to about 485 percent, based on the weight of said terpolymer, of a physiologically acceptable flake material dispersed in said terpolymer, said terpolymer in combination with said flake material being physiologically acceptable and resistant to a pH of greater than about 5 but capable of releasing the core of the pellets at a pH of less than about 3.5, and said composition having a glass transition temperature as measured by TMA of not more than about 60° C.

27. A composition according to claim 26 wherein the core comprises lysine.

28. A composition according to claim 26 wherein the glass transition temperature of the composition is between about 30° C. and about 60° C.

29. A composition according to claim 26 wherein said terpolymer has an acrylate residue derived from an acrylate monomer having the formula wherein R' is H or methyl and R" is a straight, branched or cyclic alkyl group of 1 to 20 carbon atoms.

30. A composition according to claim 29 wherein said acrylate monomer is selected from the group consisting of n-lauryl acrylate, 2-ethylhexyl acrylate, cyclohexyl acrylate, and iso-octyl acrylate.

31. A composition according to claim 29 wherein said terpolymer comprises from about 65 to about 85 weight percent of component (a)(1), from about 30 to about 5 weight percent of component (a)(2), and from about 5 to about 15 weight percent of component (a)(3).

32. A polymer comprising
  (1) from about 50 to about 95 percent by weight of a 2-vinylpyridine residue, and
  (2) from about 5 to about 50 percent by weight of two or more residues of monomers selected from the group consisting of styrene, isoprene, butadiene, and an alkyl acrylate, wherein the polymer has a glass transition temperature, as measured by differential scanning calorimetry, of from about 50° C. to about 100° C., a water transmission of from 0 to about 29 g.mil/100 inches$^2$/24 hours measured on a sovlent-cast film, and an inherent viscosity of from about 0.3 to about 2.0.

33. The polymer of claim 32 which is a terpolymer comprising
(a) from about 50 to about 95 percent by weight of 2-vinylpyridine,

(b) from about 45 to about 2 percent by weight of styrene, and
(c) from about 3 to about 20 percent by weight of a monomer selected from the group consisting of isoprene, butadiene, and an alkyl acrylate.

34. The polymer of claim 32 wherein said alkyl acrylate is of the formula wherein R' is H or methyl, and R" is a straight chain, branched or cyclic alkyl group of 1 to 20 carbon atoms.

35. The polymer of claim 33 wherein said alkyl acrylate is of the formula wherein R' is H or methyl, and R" is a straight chain, branched or cyclic alkyl group of 1 to 20 carbons atoms.

36. The polymer of claim 33 wherein component (c) is an alkyl acrylate.

37. The polymer of claim 34 wherein R" is an alkyl group of 6 to 20 carbon atoms.

38. The polymer of claim 35 wherein R" is an alkyl group of 6 to 20 carbon atoms.

39. The polymer of claim 32 wherein said alkyl acrylate is selected from the group consisting of n-lauryl acrylate, 2-ethylhexyl acrylate, cyclohexyl acrylate, and isooctyl acrylate.

40. The polymer of claim 33 wherein said alkyl acrylate is selected from the group consisting of n-lauryl acrylate, 2-ethylhexyl acrylate, cyclohexyl acrylate, and isooctyl acrylate.

41. The polymer of claim 32 wherein component (a) is present in an amount of from about 65 to about 85 weight percent, component (b) is present in an amount of from about 30 to about 5 weight percent, and component (c) is present in an amount of from about 5 to about 15 weight percent.

42. The polymer of claim 32 wherein the Tg is from about 70° C. to about 90° C., the water transmission is from 0 to about 20 g.mil/inches$^2$/24 hours, and the inherent viscosity is from about 0.8 to about 1.7.

43. The polymer of claim 33 wherein the Tg is from about 70° C. to about 90° C., the water transmission is from 0 to about 20 g.mil/inches$^2$/24 hours, and the inherent viscosity is from about 0.8 to about 1.7.

* * * * *

UNITED STATES PATENT AND TRADEMARK OFFICE
CERTIFICATE OF CORRECTION

PATENT NO. : 4,837,004
DATED : June 6, 1989
INVENTOR(S) : Stephen H.W. Wu et al.

It is certified that error appears in the above-identified patent and that said Letters Patent is hereby corrected as shown below:

Column 23, line 46, in Claim 11, "axes," should be ---waxes,---.

Column 23, line 61, in Claim 11, "60C" should be ---60°C---.

Column 24, line 4, in Claim 14, after "claim", insert ---11---.

Column 24, lines 67 and 68, in Claim 19, "carboxylic" should be ---carboxyl---.

Column 25, line 39, in Claim 21, "precent" should be ---percent---.

Signed and Sealed this

Sixth Day of March, 1990

Attest:

JEFFREY M. SAMUELS

Attesting Officer
Acting Commissioner of Patents and Trademarks